United States Patent [19]
Etheredge

[11] Patent Number: 5,333,753
[45] Date of Patent: Aug. 2, 1994

[54] FINGER BANDAGE PACKAGE AND DISPENSER

[75] Inventor: Robert W. Etheredge, Natick, Mass.

[73] Assignee: The Kendall Company, Mansfield, Mass.

[21] Appl. No.: 162,244

[22] Filed: Dec. 6, 1993

[51] Int. Cl.$^5$ .............................................. B65H 1/00
[52] U.S. Cl. ......................... 221/33; 206/441; 607/57
[58] Field of Search ................ 221/25, 33, 70; 206/441, 460, 470, 440; 602/57

[56] References Cited

FOREIGN PATENT DOCUMENTS 41248   2/1969  Finland .................. 206/441
2409210 6/1979  France ................... 602/57

*Primary Examiner*—Robert P. Olszewski
*Assistant Examiner*—Kenneth Noland
*Attorney, Agent, or Firm*—Alvin Isaacs

[57] ABSTRACT

Disclosed is a package and dispenser for a per se known finger bandage comprising an elongated backing carrying an adhesive layer on one surface thereof with an absorbent pad seated on the adhesive layer substantially intermediate the ends of the bandage, the free ends of bandage on either side of the pad being folded inwardly to significantly reduce the size of the package, the bandage being contained between opposed top and bottom sheet materials lightly adhered together around their common periphery to enclose the bandage, the bandage having release sheets covering the adhesive layer on either side of the pad, the release sheet on side of the pad being secured at its end furtherest from the pad to one of the sheet materials and the release sheet on the other side of the pad being secured at its end furtherest from the pad to the other sheet material, whereby stripping apart of the two sheet materials will also remove the release sheets from the bandage.

3 Claims, 2 Drawing Sheets

FINGER BANDAGE PACKAGE AND DISPENSER

BACKGROUND OF THE INVENTION

Finger bandages (also sometimes referred to in the art as first-aid bandages or strip bandages) are of course well known as well as having achieved wide commercial success. Such bandages typically consist of an elongated backing carrying on one side thereof a layer of a medical grade pressure-sensitive adhesive. An absorbent pad is substantially centrally disposed on the adhesive layer intermediate the ends of the bandage, leaving free adhesive on either side of the absorbent pad for securing the dressing to the skin over a wound, which free adhesive will be covered by a release sheet to avoid premature contact of the adhesive to a substrate.

The most widely used packaging means comprises individual wrappers for each bandage which must be torn open to gain access to the bandage. The release sheets are then removed and the bandage applied to the wound.

While such packaging mechanism does provide a sterile enclosure, it nevertheless suffers from certain disadvantages, chief of which are awkwardness and/or difficulty in application, especially without inadvertently touching the absorbent pad to be applied over the wound and to which a topical agent, e.g. petroleum jelly or antibiotic ointment may have been first applied.

Consequently, various packaging and dispensing means have heretofore been suggested to obviate this problem. However, primarily due to cost of manufacture, none of these packaging and dispensing means, to the best of Applicant's knowledge, have ever achieved any significant commercial success to the extent that to date the market leaders, "BAND-AID" (trademark of Johnson & Johnson) and "CURAD" (trademark of The Kendall Company) and their imitators still market their finger bandages in the manner described above, a plurality of the individually wrapped finger bandages then being packaged in an outer box or container.

While not intended to represent a comprehensive search of the art, the following patents may be taken as illustrative of the state of the art pertaining to packages for dispensing finger bandages: U.S. Pat. Nos. 2,969,144 of Zackheim; 3,018,881 of Wall; 3,347,361 of Lindeke; 4,182,449 issued to Kozlow; 4,574,951 issued to Weaver; 3,835,992 of Adams; 4,666,040 of Murata; 4,781,293 of Johns; 4,913,138 of Yoshida et al; and 5,133,477 of Etheredge (the instant Applicant) and Charkoudian.

Stated simply, the task of the present invention is to devise a cost-effective and therefore commercially feasible system for packaging and dispensing individual finger bandages and which inhibits and therefore minimizes inadvertent contact of the fingers or hand with the pad to be applied over the wound.

BRIEF DESCRIPTION OF THE INVENTION

In accordance with the present invention this task is solved in an elegant manner by providing a packaging and dispensing system wherein the bandage has the free ends on either side of the absorbent pad folded inwardly to make a significantly smaller package, the bandage being contained between opposed top and bottom sheet material lightly adhered together around their common periphery, leaving opposed ends on one side of the bandage folded outwardly and unsealed for gripping to strip the sheets apart to gain access to the bandage contained therein. The release sheet on one side of the pad is secured at its end furtherest from the pad to one of the sheets and the opposed release sheet similarly attached to the other of the sheets. Continuing pulling apart of the two sheets accordingly will remove the release sheets from the bandage as well as separating the outer wrapper from the bandage.

Because of the significant reduction in space for each individually wrapped bandage, a substantial cost saving in packaging is obtained whereby smaller outer containers housing a plurality of bandages may be employed or, alternatively a greater number of bandages may be contained in the standard outer containers currently employed.

DETAILED DESCRIPTION OF THE INVENTION

The nature and objects of the invention may best be understood by reference to the accompanying illustrative drawings taken in conjunction with the following detailed description.

Figure 1:
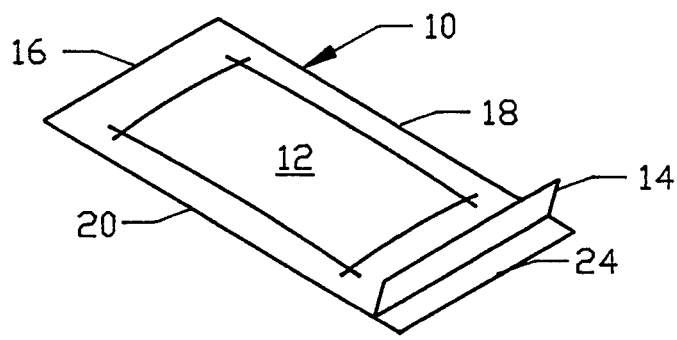
Fig. 1 is a perspective view of the finger bandage package and delivery system of this invention.
Figure 2:
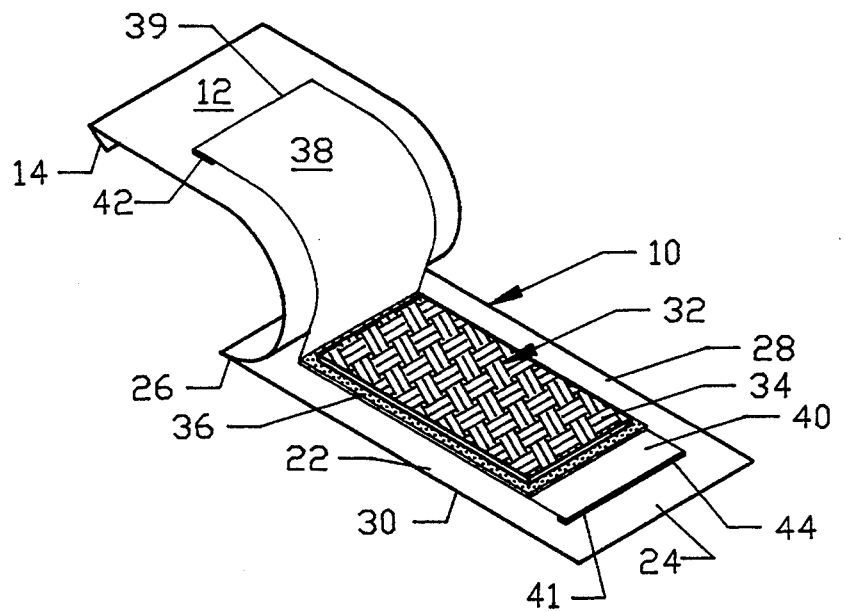
FIG. 2 is a perspective view of the package and delivery system of FIG. 1 with the cover sheet peeled back to reveal the bandage.
Figure 3:
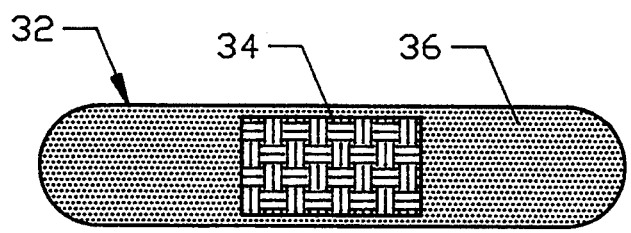
FIG. 3 is a bottom plan view of the finger bandage as removed from its package.

With reference to FIGS. 1-3, the novel package and dispenser of this invention comprises a package 10 in which the bandage 32 is contained between opposed outer sheets 12 and 22. Sheet 12 has opposed end edges 14 and 16 and opposed side edges 18 and 20; while sheet 22 has opposed end edges 24,26 and side edges 28,30. Sheets 12 and 22 are arranged with their respective end and side edges in superposition. The sheets are sealed, e.g. by means of a pressure-sensitive adhesive, to provide a sterile environment, leaving end edges 14 and 24 folded back and unsealed for gripping to open the package, as will be explained in detail hereinafter. As seen in FIG. 3, bandage 32 contained therein is a conventional finger bandage of known configuration having an absorbent pad 34 substantially centrally positioned on the adhesive surface 3 of the bandage, leaving free adhesive on either side of the pad for securing the bandage to the skin.

With reference now to FIG. 2, the ends of the finger bandage are folded over and covered with release sheets 38,40 to protect the adhesive surface from unwanted premature contact. End 39 of release sheet 38 is secured to the inner surface of sheet 12 near end 14 of sheet 12 by adhesive layer 42; and end 41 of release sheet 40 is secured to the inner surface of sheet 22 near its end 24 by adhesive layer 44.

Figure 4:
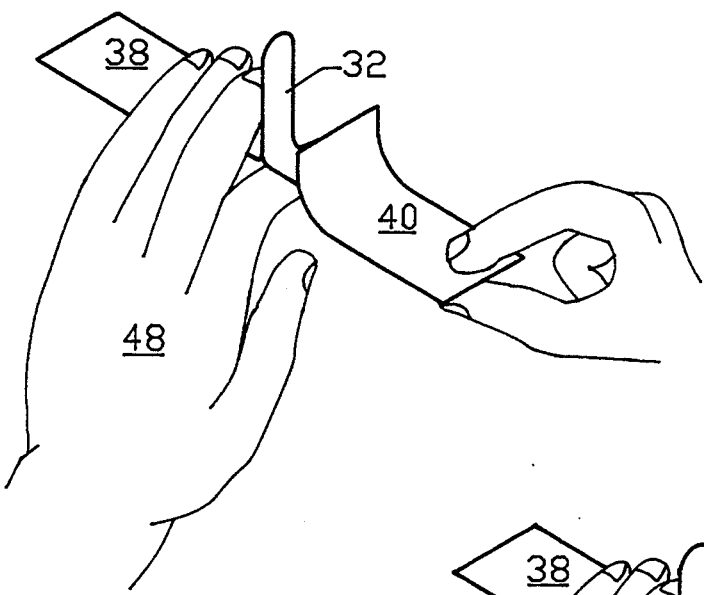
FIGS. 4–6 illustrate, sequentially, the manipulative steps for applying the bandage to a finger after the container has been opened as shown in FIG. 2.
Figure 5:
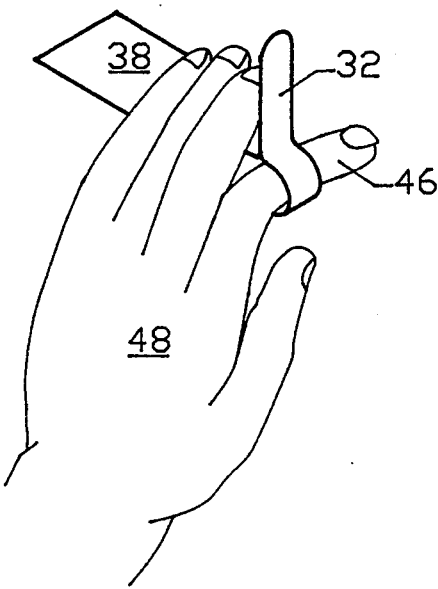
Figure 6:
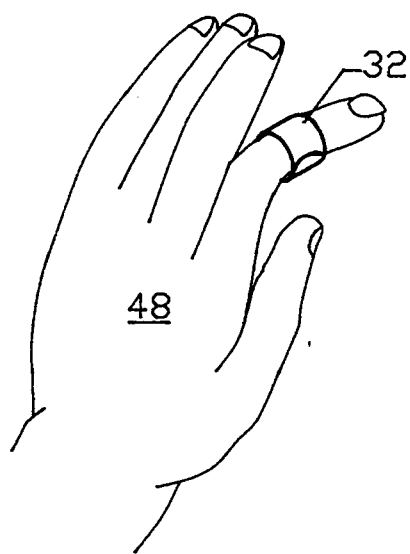

FIGS. 4–6 illustrate how the bandage is removed and wrapped around the finger while easily avoiding contact with the sterile absorbent pad 34 to be placed over a finger 46 on hand 48.

Slow and even pulling separates one end of bandage 32 from release sheet 40 so that the underlying adhesive which is revealed can engage the skin to partially wrap the bandage around finger 46 as seen in FIG. 5 while hand 48 continues to grip the release sheet 38 which is then removed while placing the underlying adhesive against the skin to complete application of the bandage, as seen in FIG. 6.

From the foregoing description, it will thus be seen that the release sheets, secured at one end to the outer sheets 12,22 serve a very important function in addition to protecting the adhesive surface of the bandage, namely providing a mechanism by first unfolding the ends of the bandage and then controlling their removal form the underlying ends of the bandage as it is applied to the skin. As is clearly seen in FIGS. 4 and 5, the fingers are at all times well spaced from the absorbent pad, thereby requiting minimal dexterity to apply the bandage to oneself without accidentally contacting the pad.

The particular material which may be employed in the practice of this invention are well known and per se comprise no part of this invention. Finger bandage 32 is conventional, as heretofore noted, including the release sheets 38,40 coveting adhesive 36 of the bandage.

Outer sheets 12,22 are conventional packaging material and may be made of paper or plastic. They may be sealed around their common periphery, as heretofore described by per se known pressure-sensitive adhesives or by heat sealing it being understood, of course, that the seal should not be aggressive with minimal effort and without danger of tearing the bandage.

Adhesives 42,44 on the other hand should be aggressive, heat sealing being preferred, to prevent separation of the release sheets from the outer sheets as they are pulled apart.

By way of recapitulation, it will be seen from the foregoing description that the present package and dispenser provides significant advantages over conventional finger bandage packages, chief of which is that it inhibits and therefore minimizes the chance of inadvertent contact of the fingers or hand with the absorbent pad while removing the bandage and attempting to apply it over the wound.

Secondly, the smaller package is a cost saving and permits packaging if more individual bandages in an outer box or container.

Further, it is much simpler to dispense the bandage and apply it to the wound.

Finally, there is less trash to throw away after the bandage is applied.

Since certain changes maybe made without departing from the scope of the invention herein contemplated, it is intended that all matter contained in the foregoing specification and drawings be taken as illustrative and not in a limiting sense.

What is claimed is:

1. A finger bandage package and dispenser comprising:

a finger bandage having opposed ends and consisting essentially of an elongated backing carrying on one side thereof a layer of a medical grade pressure-sensitive adhesive and an absorbent pad adapted for placement over a wound substantially centrally disposed on the adhesive layer intermediate the opposed ends of the bandage;

a first release sheet having opposed first and second end edges covering the adhesive layer on one side of the pad;

a second release sheet having opposed first and second end edges and covering the adhesive layer on the opposite side of the pad;

a first sheet material having first and second opposed end edges and opposed first and second side edges;

a second sheet material having first and second opposed end edges and first and second opposed side edges;

the ends of the finger bandage being folded inwardly whereby to make a significantly smaller package;

the first and second sheet materials being placed in superposition with the first end edge of each sheet material in superposition and the finger bandage being contained between the superposed sheet materials with the second end edges of the release sheets adjacent the superposed second end edges of the sheet materials;

the superposed sheet materials being lightly sealed together around their opposed side edges and their first end edges, their respective second end edges being unsealed, the superposed sheet materials defining an outer wrapper for the bandage contained therebetween;

the first end edge of the first release sheet being secured to the first sheet material nearest the first end edge of the first sheet material;

the second end edge of the second release sheet being secured to the second sheet material nearest the second end edge of the second sheet material; and means at the opposed unsealed end edges of the sheet materials for gripping the sheet materials to strip them apart to gain access to the finger bandage contained therein, whereby continued pulling apart of the two sheet materials will remove the release sheets from the bandage as well as to separate the outer wrapper to free the finger bandage from within.

2. A finger bandage package and dispenser as defined in claim 1 wherein the gripping means comprises the unsealed opposed second end edges of the sheet materials being folded outwardly for gripping.

3. A finger bandage as defined in claim 1 wherein the sheet materials are sealed together around their opposed side edges and their first end edges by a pressure-sensitive adhesive.

* * * * *